US007939112B2

(12) United States Patent
Barthel

(10) Patent No.: US 7,939,112 B2
(45) Date of Patent: May 10, 2011

(54) PHARMACEUTICAL COMPOSITIONS CONTAINING BULBOPHYLLUM AND THEIR USE FOR TREATING ILLNESSES

(76) Inventor: Michael Barthel, Nendeln (LI)

( * ) Notice: Subject to any disclaimer, the term of this patent is extended or adjusted under 35 U.S.C. 154(b) by 361 days.

(21) Appl. No.: 12/078,980

(22) Filed: Apr. 9, 2008

(65) Prior Publication Data

US 2008/0213405 A1 Sep. 4, 2008

Related U.S. Application Data

(60) Division of application No. 11/508,307, filed on Aug. 23, 2006, now abandoned, which is a continuation of application No. 10/475,493, filed as application No. PCT/EP02/04655 on Apr. 26, 2002, now Pat. No. 7,118,769.

(30) Foreign Application Priority Data

Apr. 26, 2001 (DE) .................................. 101 20 630

(51) Int. Cl.
*A61K 36/00* (2006.01)
(52) U.S. Cl. ...................................................... 424/725
(58) Field of Classification Search .................... None
See application file for complete search history.

(56) References Cited

U.S. PATENT DOCUMENTS

| 5,750,107 | A | 5/1998 | Nomura |
| 6,503,552 | B1 * | 1/2003 | Rao et al. ........................ 426/541 |
| 7,118,769 | B2 * | 10/2006 | Barthel ............................. 424/725 |
| 2004/0156920 | A1 * | 8/2004 | Kane ................................ 424/725 |

FOREIGN PATENT DOCUMENTS

| EP | 0 627 213 B1 | 3/1998 |
| JP | 07070942 A | 3/1995 |

OTHER PUBLICATIONS

Wesite document from MedicineNet.com entitled "Medications and Drugs" obtained from the website http://www.medicinenet.com/nifedipine-oral/article.htm, downloaded on Jun. 22, 2010, 4 pages.*
Changkija, S., "Folk Medicinal Plants of the Nagas in India", *Asian Folklore Studies: Research Notes*, vol. 58, pp. 205-230, (1999). XP009078233.
Rajendran, A., et al., "Some Useful Rare and Endemic Plants of the Southern Western Ghats", *J. Econ. Taxon. Bot.*, vol. 26, No. 1, pp. 181-184, (2002).
"*Bulbophyllum nudum* Thouars" *Papua New Guinea Orchid News*, Abstract Only, www.orchidspng.com/Bulbophyllum.html; researched Dec. 6, 2001.
Majumder, P.L., et al., "Bibenzyl derivatives from the orchid *Bulbophyllum protactum*", Phytochemistry (Oxford) vol. 44, No. 1, pp. 167-172, (1997), Database Biosis, AB 1997:71219. Abstract only.
Piironen, Vieno, et al., "Plant sterols; biosynthesis, biological function and their importance to human nuitrition" *J. Sci. Food Agri.* vol. 80 (7), pp. 939-966, (2000), Database CAPLUS AN 2000:352618. Abstract only.
Leong, Y-W., et al., "Phenanthrenes, dihydrophenanthrenes and bibenzyls from the orchid *Bulbophyllum vaginatum*" *Phytochemistry* (Oxford), vol. 44, No. 1, pp. 157-165, (1997), Database BIOSIS, AN 1997:71281. Abstract only.
Majumder, P.L. et al., "Cumulatin and tristin, two bibenzyl derivatives from the orchids *Dendrobium cumulatum* and *Bulpophyllum triste*" Phytochemistry (Oxford), vol. 32, No. 6, pp. 1561-1565, (1993), Database BIOSIS, AN 1993:27927. Abstract only.
Rajndran et al, "Some Medicinal Orchids of Southern India," Ancient Science of Life 1997, vol. 17(1): 10-14.

* cited by examiner

*Primary Examiner* — Christopher R. Tate
(74) *Attorney, Agent, or Firm* — The Nath Law Group; Tanya E. Harkins

(57) ABSTRACT

Described are pharmaceutical compositions containing *Bulbophyllum*, in particular compositions containing *Bulbophyllum neilgherese*, optionally in combination with suitable pharmaceutical excipients and carriers, as well as their use for treating illnesses, in particular illnesses of the cardio-vascular system.

6 Claims, No Drawings

PHARMACEUTICAL COMPOSITIONS CONTAINING BULBOPHYLLUM AND THEIR USE FOR TREATING ILLNESSES

This Application is a Divisional of U.S. patent application Ser. No. 11/508,307, filed on Aug. 23, 2006, which was a Continuation of U.S. patent application Ser. No. 10/475,493, filed on Mar. 15, 2004, now U.S. Pat. No. 7,118,769, which was a 371 of PCT/EP2002/004655, filed on Apr. 26, 2002, the entire content of which is hereby incorporated by reference in its entirety.

The present invention relates to pharmaceutical compositions containing *Bulbophyllum*, particularly *Bulbophyllum neilgherense*, and its use for treating illnesses, in particular illnesses of the cardio-vascular system.

There is a considerable need for the development of drugs and medicaments, respectively, having good effectiveness and large indication indexes as well as little or no side effects, to augment the present therapies of cardio-vascular illnesses.

Surprisingly, this object could be successfully achieved by providing the pharmaceutical compositions containing *Bulbophyllum* described below.

U.S. Pat. No. 4,691,472 relates to the cultivation of Epiphytes, especially orchids. *Bulbophyllum* is stated as one example of an orchid genus.

So far, *Bulbophyllum* extracts have only been disclosed in EP-0 627 213. Here, a cosmetic formulation for the promotion of hair growth is described, said formulation containing an extract from orchid plants, i.a. *Bulbophyllum*.

In the light of this state of the art, it was completely unexpected to discover that the plant species *Bulbophyllum* shows the pharmacological effects described below, making it especially useful for the treatment of cardio-vascular diseases.

The following description illustrates in detail the pharmacological test results which led to the above conclusions, as well as specific cardio-vascular indications.

*Bulbophyllum neilgherense* is a member of the orchidaceae family. It is an epiphyte that grows on broadleaf trees, more specifically on taller rain forest trees. The rhizome is thick and of creeping growth. The pseudo-bulb is 3-5×2-2.5 cm, conical-ovate, tapering off in a solitary leaf. This leaf is 4-11×1.8-2.2 cm, elliptically-oblonged, narrowed at its base. The flowers are brown, sometimes with a purple shade, and reside in a panicle 7-12 cm long, emanating from the pseudo-bulb's base. The peduncles are 3-4 mm long. The spatheceous bract of the inflorescence is 5-6 mm long, inverted lanceolate. The dorsal sepals are 4-5 mm long, ovate and concave. The lateral sepals are 7-8 cm long, of scimitar-shape, their accreted inner rims forming a concave, cymbiform structure. The petals are 3-3.5-mm long, triangular-ovate. The flower lips are 5-6 mm long, reddish, three-lobed; the middle lobe is prolonged and ovate-lanceolate, the lateral lobes are linear. There are 4 anthers of waxen appearance. The plant is common all over South-West India.

For the drugs according to the present invention predominantly the main part of the plant is used, i.e. the entire bulb without the appending roots and without protruding leaf.

In this description, the term drugs refers to dried or otherwise processed parts of plants (herbal drugs) which are used for medical preparations. Furthermore, it includes certain raw products extracted from these plants (e.g. fatty and ethereal oils, resins, balsams and gums).

Drug preparations which comprise an accumulation of active substances include, but are not limited to: extracts, paints, percolates, macerates, infusions, pressed juices, decoctions (tea), distillates. Drug ingredients refers to the sum of chemical components that characterize a drug, i.e. therapeutically active substances as well as accompanying or inert substances without innate therapeutical action, such as cellulose, starch, waxes. The latter usually make for the bulk of extra substances.

The plant that is useful for the preparation of drugs can be harvested from its natural habitat, or artificially grafted onto other trees, or grown in green houses.

When working up the plant, conventional techniques can be employed, e.g. purification, milling and drying, as well as stabilization processes. One preferred example of drying techniques is lyophilization.

Due to the fact that neither the plant itself nor the drug deteriorate during long time transports or under the exposure of tropical heat, freeze-drying and processing can be postponed.

The pharmaceutical composition or the drug, respectively, can be prepared in various ways using common techniques, but preferably as triturations with milk sugar or alcoholic extracts. When prepared as alcoholic extracts, the alcohol content by volume is 80 to 100%, preferably 94 to 98%, even more preferred 96%.

The drug content of said extract or said trituration per single dose is preferably 1 ng to 1 mg, even more preferred 10 ng to 1 mg.

Preferably, the drug is administered as 1 to 3 daily doses over a period of 1 to 12 months, preferably 2 to 5 months, more preferred 3 to 4 months. Alternatively, the administration of single doses with intervals of 1 day to 12 months, more preferred 3 to 4 months, can be sufficient to achieve the desired effect according to the present invention.

A person skilled in the art will be able to determine and appropriately adjust the adequate dosage for achieving the optimum therapeutic effect.

Pharmaceutical Administration Forms

Pharmaceutical compositions containing *Bulbophyllum* according to the present invention are prepared and administered according to conventional methods using common pharmaceutical technologies.

For this purpose, the drug, or preferably its extraction or trituration, is processed together with suitable pharmaceutically acceptable excipients and carriers to prepare drug forms that can be used for various indications and application sites.

One important systemic form of application is the peroral application of tablets, hard or soft gelatine capsules, dragées, powders, pellets, micro capsules, oblonged comprimates, granulae, chewing tablets, sucking tablets, chewing gums, sachets, or globuli.

Excipients that are used for the preparation of perorally administered pharmaceutical compositions are e.g. antiadhesives, lubricants and anticaking agents, dispersants, such as flame hydrolyzed disperse silica, disintegrants, such as various types of starches, PVP, cellulose esters acting as granulating agents, such as ceraceous and/or polymeric substances on the basis of Euthragit™, cellulose or Cremophor™.

Other ingredients that can be used are antioxidants, sweetening agents, such as saccharose, xylitol or mannite, taste corrigents, flavors, preservatives, colorants, buffers, direct application vehicles, such as microcrystalline cellulose, starch and hydrolyzed starch (e.g. Celutab™), milk sugar, polyethylene glycol, polyvinyl pyrrolidone and dicalcium phosphate, lubricants, fillers, such as lactose and starch, binders consisting of lactose, certain kinds of starch, e.g. wheat, corn or rice starch, cellulose derivatives, such as methyl cellulose, hydroxypropyl cellulose or siliceous earth, talcum, stearates, such as magnesium stearate, aluminium stearate, calcium stearate, talc, siliconized talc, stearic acid, cetyl alcohol, hydrogenated fats.

Examples of common skin application forms are the conventional emulsions, gels, ointments, creams, or mixed phase or amphiphilic emulsion systems (oil-in-water/water-in-oil mixed phases), as well as liposomes and transferosomes. Their epidural application is also preferred.

Examples for suitable excipients or carriers are sodium alginate that acts as gel forming agent for the preparation of an appropriate base, or cellulose derivatives, such as guar or xanthan gum, anorganic gel forming agents, such as aluminium hydroxide or bentonite (so-called thixotropic gel forming agents), polyacrylic acid derivatives, such as Carbopol™, polyvinyl pyrrolidone, microcrystalline cellulose or carboxymethyl cellulose. Amphiphilic compounds of low or high molecular weight, such as phospholipids, can also be taken into consideration. These gels can exist as water-based hydrogels or as hydrophobic organogels, e.g. on the basis of admixtures of paraffin hydrocarbons of low or high molecular weight and vaseline.

Suitable emulsifiers that can be used for the preparation of oil-in-water or water-in-oil emulsions are anionic, cationic or neutral surfactants, such as alkaline soaps, metal soaps, amino soaps, sulfurized and sulfonized compounds, invert soaps, high fatty alcohols, partial esters of sorbitan or polyoxyethylene sorbitan fatty acids, wool wax, lanolin, among other synthetic products.

Hydrophilic organogels can e.g. be prepared on the basis of polyethylene glycol of high molecular weight. These gel-like forms can be washed off. Lipids consisting of fatty and/or oily and/or waxy components useful for the preparation of ointments, creams or emulsions are e.g. vaseline, natural or synthetic waxes, fatty acids, fatty alcohols, fatty acid esters, such as mono-, di-, or triglycerides, paraffin oil or vegetable oil, hydrogenated castor oil or coconut oil, lard, synthetic fats, e.g. on the basis of caprylic acid, capric acid, lauric acid and stearic acid, or mixtures of triglycerides, such as Miglycol™.

For pH adjustments, osmotically active acids and alkalis can be used, such as hydrochloric acid, citric acid, sodium hydroxide solutions, potassium hydroxide solutions, sodium hydrogen carbonate, as well as buffer systems, such as citrate, phosphate, tris-buffers or triethanol amine.

Furthermore, preservatives, such as methyl or propyl benzoate (parabene), or sorbic acids can be added to enhance stability.

Other examples for topic application forms are pastes, powders or solutions. The pastes often contain very high solid lyophilic and hydrophilic excipients that serve as bases for providing consistency. For the improvement of dispersity, fluidity and glide-ability, as well as for agglomerate prevention, the dustable or topically applicable powders can contain e.g. various types of starches, such as wheat or rice starch, flame hydrolyzed disperse silica or siliceous earths that can also serve as dilutants.

Preferred transdermal systems that are able to controllably release the active substances over short or prolonged periods of time are plaster preparations consisting of several layers and/or mixtures of suitable excipients and carriers. To enhance or accelerate penetration, various substances can be added during the preparation of said transdermal systems in order to promote membrane permeation, e.g. permeation promoters, such as oleic acid, Arzone™, adipic acid derivatives, ethanol, urea, propyl glycol, as well as suitable excipients and carriers, such as solvents, polymeric components, e.g. on the basis of Euthragit™.

The plasters are preferably applicated in the precordial area.

A further administration method uses injectables. They are prepared either as ampoules or so-called ready-to-use injectables, such as syrettes or disposable syringes, and also punctable containers for multiple withdrawals. Said injectables can be applied subcutaneous (s.c.), intramuscular (i.m.), intravenous (i.v.), or intracutaneous (i.c.). The specific convenient injection form can be prepared as solutions, suspensions of crystals, or nanoparticulate or collidal-diperse systems, such as hydrosols.

The injectables can also be prepared in the form of concentrates, whose active substance content can be adjusted using water-based isotonic dilutants. Furthermore, they can be prepared as powders, such as lyophilisates, that are only solved or dispersed immediately before application.

Excipients and carriers that can be used for injectable preparations are sterilized water, pH controlling substances, such as organic and inorganic acids and alkalis as well as their salts, buffers for adjusting the pH value, isotonicity agents, such as sodium chloride, sodium hydrogen chloride, glucose and fructose, surfactants or surface-active substances, respectively, and emulsifiers, such as partial fatty acid esters of polyoxy-ethylene sorbitan (Tween™) or fatty acid esters of polyoxyethylene (Cremophor™), fatty oils, such as groundnut oil, soy bean oil and castor oil, synthetic fatty acids esters, such as ethyl oleate, isopropyl myristate and neutral oil (Miglycol™) as well as polymeric excipients, such as gelatine, dextrane, polyvinyl pyrrolidone, solubility increasing additives consisting of organic solvents, such as propylene glycol, ethanol, N,N-di-methyl acetamide, propylene glycol or complex forming substances, such as citrates and urea, preservatives, such as the hydroxy propyl and methyl esters of benzoic acid, benzyl alcohol, antioxidants, such as sodium sulfite, and stabilizing agents, such as EDTA.

The drugs can also be administered perlingually.

Delayed release administration forms can also be applied.

A person skilled in the art will readily be able to identify and prepare the adequate drug forms in accordance with prescriptions and processing methods on the basis of pharmaceutical/physical knowledge.

Indication Areas

The pharmaceutical composition containing *Bulbophyllum* according to the present invention is useful for treating all disorders of the cardio-vascular system, especially in case of cardiopathy in family history, unusual perception of the heart, cardiac condition related anxiety, chest tightness, chest pressure, bradycardia, tachycardia, extrasystoles, arrhythmia, palpitation, atrial fibrillation, cardialgia, stabbing heart pains, sternum pains, heart pains radiating into the left arm and tingling sensation in the left arm, angina pectoris, stenosis of the coronary arteries, myocardial infarct, cardiac insufficiency involving edemas, myocardial and septal hypertrophy, right ventricle cardiomegaly, ventricle septum defect, atrium septum defect, primary pulmonary hypertension, hypertonia, peripheral acral cyanosis, lip cyanosis, dyspnea, exertional dyspnea, altitude intolerance, coronaria related hot flushes, disturbed blood flow in the limbs caused by heart insufficiency, cold limbs, physical weakness caused by heart insufficiency, reduced ability, weak condition following rheumatic fever, valvular disorders, cardiopathic difficulties falling asleep, insomnia, cardiopathic cough.

Pharmacological Test Section

In the course of 3 years, 127 patients were treated with the pharmaceutical composition according to the present invention. 61 of these patients were women (49%). Among these 127 patients, 82 individuals recovered to a considerable extent or even completely. Among these 82 patients, 31 individuals experienced a resounding subjectively and objectively observed recovery.

Each of said 127 patients was given one single dose. During the effective period of said single dose no other medicaments were administered, as well as no vitamins, trace elements, minerals, physiotherapeutics etc.

For said 82 patients who had recovered considerably or completely, the single dose administration had to be repeated only after 7 weeks. The longest duration of effect was 11 months, i.e. only after 11 months did these patients experience the recurrency of ailments that required another dose. The average duration of effect of a single dose was three to four months. This single dose duration of effect varies with the severity of the disorder.

Comparison with Other Heart Therapeutics in Terms of Potence, Side-Effects, Duration and Cost Effectiveness When compared to the pharmaceutical composition containing *Bulbophyllum* according to the present invention, no other heart therapeutic possesses a similar indication index and activity range.

Due to the fact that the administration is done in a doctor's practice and no subsequent administration is necessary until the recurrence of the patient's ailments, no other heart therapeutic has a compliance as high as the pharmaceutical compositions containing *Bulbophyllum* according to the present invention.

Most patients recovered without a preceding aggravation of symptoms. Approximately 5% of the group experienced a mild aggravation that lasted no longer than three to five days. Approximately 15% of the group experienced a short-term aggravation of symptoms emerging during the third week after administration, after a few hours or a few days without further administration, however, the symptoms had eased.

None of the examined patients developed any side-effects.

No other heart therapeutic has such long duration of effect.

Furthermore, the cost of treatment with the extract according to the present invention is only ⅙ of conventional heart therapeutics, e.g. Niphedipin (Adalat).

Due to the fact that most patients suffering from heart disease are multimorbid, the costs for treating their ailments with additional therapeutics would have to be added in case of conventional therapies with state of the art drugs. In case of the *Bulbophyllum* therapy, no other medicament was administered to the patient. Consequently, the costs for other therapeutics are eliminated, which leads to a still better performance of *Bulbophyllum* in terms of cost effectiveness.

I claim:

1. A method of treating a cardiovascular disease selected from the group consisting of chest tightness, chest pressure, bradycardia, tachycardia, extrasystoles, arrhythmia, palpitation, atrial fibrillation, angina pectoris, stenosis of the coronary arteries, myocardial infarct, myocardial and septal hypertrophy, right ventricle cardiomegaly, primary pulmonary hypertension, hypertonia, peripheral acral cyanosis, dyspnea, and extertional dyspnea, the method comprising:

administering to a patient suffering from said cardiovascular disorder a composition comprising an effective amount of *Bulbophyllum neilgherense* in combination with a pharmaceutically acceptable excipient and/or carrier.

2. The method according to claim 1, wherein said composition is in the form of an alcoholic extract.

3. The method according to claim 2, wherein the alcoholic extract has an alcohol content of 81% to 100% by volume.

4. The method according to claim 1, wherein said composition is administered in one to three daily doses over a period of one to ten months.

5. The method according to claim 1, wherein the effective amount of *Bulbophyllum neilgherense* per single dose is in the range of 1 ng to 1 mg.

6. The method according to claim 1, wherein the composition is administered epidurally, perorally, or topically.

* * * * *